United States Patent [19]

Ito et al.

[11] Patent Number: 4,822,350

[45] Date of Patent: Apr. 18, 1989

[54] ABSORBENT ARTICLE

[75] Inventors: Osamu Ito, Utsunomiya; Hiroshi Mizutani, Yachiyo, both of Japan

[73] Assignee: Kao Corporation, Tokyo, Japan

[21] Appl. No.: 823,469

[22] Filed: Jan. 28, 1986

[30] Foreign Application Priority Data

Jan. 30, 1985 [JP] Japan .................................. 60-15754
Oct. 25, 1985 [JP] Japan ................................. 60-239122

[51] Int. Cl.$^4$ ............................................ A61F 13/16
[52] U.S. Cl. ..................................... 604/372; 604/370
[58] Field of Search ............... 604/358, 365, 366, 367, 604/370, 371, 372, 373, 378, 381, 382

[56] References Cited

U.S. PATENT DOCUMENTS

| | | | |
|---|---|---|---|
| 3,426,754 | 2/1969 | Bierenbaum et al. | 604/370 |
| 3,843,478 | 10/1979 | Zuscik | 604/370 |
| 3,989,867 | 11/1976 | Sisson | 604/370 |
| 4,166,464 | 9/1979 | Korpman | 604/372 |
| 4,304,234 | 12/1981 | Hartmann | 604/372 |
| 4,341,216 | 7/1982 | Obenour | 604/370 |
| 4,381,326 | 4/1983 | Kelley | 604/370 |
| 4,447,570 | 5/1984 | Cook et al. | 604/367 |
| 4,535,020 | 8/1985 | Thomas et al. | 604/383 |

FOREIGN PATENT DOCUMENTS 2115702  9/1983  United Kingdom .

*Primary Examiner*—John D. Yasko
*Assistant Examiner*—Denise Whelton
*Attorney, Agent, or Firm*—Birch, Stewart, Kolasch & Birch

[57] ABSTRACT

In an absorbent article which comprises a liquid-impermeable, leakproof sheet, a liquid-permeable surface sheet and an absorbent layer, the leakproof sheet is a porous film, monoaxially or biaxially stretched, of a polyolefin resin composition comprising a polyolefin and a filler, having a thickness of not larger than 60 microns, an average pore size of 0.05 to 5 microns, a pore volume of not smaller than 0.1 cm$^3$ per 1 cm$^3$ of the film, a water vapor permeability of not smaller than 500 g/m$^2$ for 24 hours and a bending resistance at either longitudinal or transversal directions to meet the following definition:

a bending resistance (mm)=0.193× a film thickness (micron)×35.

9 Claims, No Drawings

ABSORBENT ARTICLE

This invention relates to an absorbent article such as a one-piece disposable diaper or a sanitary napkin. More specifically, the invention relates to an absorbent article using as the leakproof sheet a liquid-impermeable, vapor-permeable porous film.

Prior Arts and Problems

A film prepared by admixing 3 to 5% of titanium oxide with polyethylene, forming therefrom a film having a basis weight of 20 to 30 g/m², and embossing the film, has heretofore been employed as a leakproof sheet of an absorbent article such as a disposable diaper or a sanitary napkin. However, such a film is impermeable to water vapor. Therefore, when the absorbent article is worn for a long time, the state of stuffiness ensues, and a rash caused by a diaper or the like is likely to appear. Although the use of a porous film is disclosed in Japanese Patent Laid-Open No. 149,303/1983, a biaxially stretched film among others is not necessarily satisfactory in flexibility, while a monoaxially stretched film unsatisfactorily tends to be low in transversal strength.

SUMMARY OF THE INVENTION

In an absorbent article which comprises a liquid-impermeable, leakproof sheet, a liquid-permeable surface sheet and an absorbent layer, the leakproof sheet used in the invention is a porous film, monoaxially or biaxially stretched, made of a polyolefin resin composition comprising a polyolefin and a filler, which has a thickness of not larger than 60 microns, an average pore size of 0.05 to 5 microns, a pore volume of not smaller than 0.1 cm3 per 1 cm3 of the film, a water vapor permeability of not smaller than 500 g/m2 for 24 hours and a bending resistance at either longitudinal or transversal directions to meet the following definition:

a bending resistance (mm)=0.193×a film thickness (micron)+35.

The leakproof sheet is preferred to have an Elmendorf tear strength in the longitudinal direction of not smaller than 15 kg·cm/cm2.

A first, preferable embodiment is a leakproof sheet which has been biaxially stretched and has a thickness of not larger than 45 microns and an Elmendorf tear strength in the longitudinal direction of not smaller than 15 kg·cm/cm2. In other words, a first embodiment is an absorbent article preferably comprises a liquid-impermeable, leakproof sheet, a liquid-permeable surface sheet, and an absorbent layer provided between both the sheets, characterized in that said leakproof sheet is a porous film obtained by biaxially stretching a film prepared by melt-extruding a polyolefin resin composition containing a filler, which has a thickness of 45μ or less, an average pore size of micropores of 0.05 to 5μ, a pore volume of 0.1 cm³ or more per unit volume of film of 1 cm³, a water vapor permeability of 500 g/m²·24 hr or more, an Elmendorf tear strength in the longitudinal direction of said film of 15 kg·cm/cm² or more, and such bending resistances, in both the longitudinal and transversal directions, as to satisfy the following formula (1):

$$\text{bending resistance} \leq 0.193 \times \text{film thickness} + 35 \qquad (1)$$

(wherein the unit of bending resistance is mm, and the unit of film thickness is μ).

A second, preferable embodiment of the leakproof sheet has been monoaxially stretched. In other words, a second embodiment is an absorbent article preferably comprises a liquid-impermeable, leakproof sheet, a liquid-permeable surface sheet, and an absorbent layer provided between both the sheets, characterized in that said leakproof sheet is a porous film obtained by monoaxially stretching a film prepared by melt-extruding a polyolefin resin composition containing a filler, which has a thickness of 60μ or less, an average pore size of micropores of 0.05 to 5μ as measured with a mercury porosimeter a pore volume of 0.1 cm³ or more per unit volume of film of 1 cm³, a water vapor permeability of 500 g/m²·24 hr or more, and such bending resistances in both the longitudinal and transversal directions, as to satisfy the following formula (1):

$$\text{bending resistance} \leq 0.193 \times \text{film thickness} + 35 \qquad (1)$$

(wherein the unit of bending resistance is mm, and the unit of film thickness is μ).

The polyolefin resins which can be used in the leakproof sheet of the absorbent article of this invention include high-density polyethylene, medium-density polyethylene, linear low-density polyethylene, or mixtures thereof. The melt index of the polyethylene is preferably in a range of 0.01 to 10 g/10 min (measured with 2.16 kg at 190° C. in accordance with ASTM D 1238-70).

The linear low-density polyethylene is a copolymer of ethylene and other α-olefin(s) and, hence, different from low-density polyethylene produced according to the conventional high-pressure process.

When the melt index of the polyethylene is lower than 0.01 g/10 min or higher than 10 g/10 min, the extrudability in molding a raw sheet by means of melt-extrusion molding becomes poor and the stability of molding is reduced. The polyethylene may be mixed with branched low-density polyethylene produced according to the high-pressure process.

Also, crystalline polypropylene may be used. Examples of such crystalline polypropylene are a homopolymer of propylene and copolymers of propylene with other α-olefins, used alone or as mixtures thereof.

An inorganic or organic filler is used. Examples of the inorganic filler include calcium carbonate, talc, clay, kaolin, silica, diatomaceous earth, magnesium carbonate, barium carbonate, magnesium sulfate, barium sulfate, calcium sulfate, aluminum hydroxide, magnesium hydroxide, zinc oxide, calcium oxide, magnesium oxide, titanium oxide, alumina, mica, asbestos powder, glass powder, "Shirasu" (white sandy sediment) baloons, zeolite, and silicate clay. Examples of the organic filler include cellulose powders such as wood powder and pulp powder. They may be used alone or as mixtures thereof.

The average particle size of the filler is preferably 30μ or less, more preferably 10μ or less, most preferably 5μ or less. When the particle size is too large, the denseness of pores in the oriented film is unfavorably poor.

The surface treatment of the filler is preferably made from the viewpoints of dispersibility of the filler into the resin and orientation of the film.

Treatment with a fatty acid or its metallic salt provides desired results.

The porous film to be used in the present invention is basically composed of a polyolefin resin and a filler and desirably includes a liquid or waxy hydrocarbon polymer, or a mixture of such a hydrocarbon polymer and an epoxy group-containing organic compound for providing flexibility. Liquid polybutadiene, liquid polybutene, liquid polyisoprene, and derivatives thereof may be used as the liquid or waxy hydrocarbon polymer. Among them, liquid polybutadiene terminated with carboxyl or hydroxyl groups is preferably used. Derivatives of liquid polybutadiene terminated with hydroxyl groups, such as those modified with an isocyanate, maleic anhydride, or epoxy groups, may also be used.

Further, liquid hydrogenated polybutadiene prepared by hydrogenating liquid polybutadiene and polyhydroxy saturated hydrocarbons prepared by hydrogenating terminal hydroxyl group liquid polybutadiene may be used. The polyhydroxy saturated hydrocarbon is a hydrocarbon polymer having a saturated or mostly saturated main chain having at least 1.5 hydroxyl groups per molecule. The number-average molecular weight of the polyhydroxy saturated hydrocarbon is preferably 400 to 20,000, more preferably 500 to 10,000. Further, terminal carboxyl hydrogenated polybutadiene may be used.

Examples of the epoxy group-containing organic compound include epoxidized vegetable oils such as epoxidized linseed oil and epoxidized soybean oil, and epoxy resins, preferably liquid epoxy resins which contains no curing agent.

Blending of an epoxy group-containing organic compound serves to improve the weather resistance particularly the resistance to weather involving NOx. Disposable diapers and sanitary napkins are often displayed in shop fronts. In such cases, the leakproof sheets of the diapers or napkins sometimes turn yellow, thus presenting a problem. Thus these problems have been solved by blending the epoxy group-containing organic compound.

According to the customary method, a heat stabilizer, an ultraviolet stabilizer, an antistatic agent, a pigment, a fluorescent agent, etc. may be added to the above-mentioned polyolefin resin.

The blending proportions of the polyolefin resin, the filler, and the liquid or waxy hydrocarbon polymer, and, further, the epoxy group-containing organic compound are as follows. 100 weight parts of the polyolefin resin is blended with 25 to 400 weight parts, preferably 50 to 250 weight parts, of the filler and 1 to 100 weight parts, preferably 3 to 70 weight parts, of the liquid or waxy hydrocarbon polymer. In the first embodiment of the leakproof sheet, up to 100 weight parts, preferably 70 weight parts, of the epoxy compound may be blended with the hydrocarbon polymer. In the second embodiment, up to 99 weight parts, preferably from 3 to 70 weight parts, of the epoxy compound may be used. It is advisable that the total amount of both hydrocarbon polymer and epoxy compound ranges from 1 to 100 parts by weight, more preferably from 3 to 70 parts by weight. When an amount of the filler is lower than 25 weight parts, pore formation in the biaxially stretched film is not sufficient and the porosity is low. When the proportion of the filler exceeds 400 weight parts, kneadability, dispersibility, and film formability become poor.

When the amount of the liquid or waxy hydrocarbon polymer or the total amount of the hydrocarbon polymer and the epoxy group-containing organic compound exceeds 100 weight parts per 100 weight parts of the polyolefin resin, the characteristics of the polyolefin resin are so damaged that satisfactory kneadability, film formability, and stretchability. cannot be secured. On the other hand, when it is less than 1 weight part, the film formability and the stretchability are so poor that a satisfactory porous film cannot be obtained.

In order to impact weather resistance, particularly resistance to weather involving Nox to a film, the amount, per 100 weight parts of the polyolefin resin, of the epoxy group-containing organic compound must be at least 1 weight part, whereas it must not exceed 99 weight parts from the viewpoint of film formability.

In the production of the leakproof sheet according to the present invention, the above-mentioned raw materials are mixed according to a known method, and formed into a film or sheet by using a usual film forming apparatus according to a usual film forming method. Specifically, inflation molding with a circular die, T die extrusion molding with a T die, or the like may be adequately adopted.

Although monoaxial stretching may be conducted with emphasis put on stretching in the monoaxial direction (in the winding direction) according to tubular stretching, roll stretching is usually preferred. The stretching ratio is preferably in a range of 1.2 to 6.

The film thickness must be $60\mu$ or less from the standpoints of economy and flexibility. Too thin a film has unpractical inferior in mechanical properties. Thus a film thickness of $10\mu$ or more is preferred.

Biaxial stretching may be conducted either consecutively or simultaneously in the longitudinal and transversal directions. The stretching ratio is preferably in a range of 1.2 to 6 in both the longitudinal and the transversal directions. The overall stretching ratio is 3 or more, preferably 3.5 or more, more preferably 4 or more from the viewpoint of physical properties.

The consecutive stretching may be carried out first in the longitudinal direction and then in the transversal direction, or vice versa. Roll stretching, tenter stretching, or tubular stretching may be adequately adopted as the stretching method.

For example, a film obtained by inflation molding or T-die extrusion molding may be longitudinally stretched by a roll and then transversally stretched by a tenter. Alternatively, a film obtained by inflation molding may be longitudinally stretched by a roll and then transversally stretched according to the tubular method, or vice versa. Further alternatively, simultaneous biaxial stretching may be effected according to the tenter or tubular method. Stretching may be effected either in one step or in multiple steps, such as two or more steps, in longitudinal as well as transversal directions. A heat treatment may be further effected to stabilize the dimensional accuracy of the film obtained by stretching.

The film or sheet thus obtained is excellent in water vapor and gas permeabilities since it has open cells. When the film as mentioned above is utilized as the leakproof sheet of an absorbent article, consideration must be given to flexibility, strength, and economy, which are greatly affected by the thickness of the film. A film thickness of $45\mu$ or less is necessary from the standpoints of economy and flexibility. However, too thin a film results in not only unpractically low strength and poor mechanical properties but also insufficient windability when winding the film after stretching thereof. Thus the film thickness is preferably $5\mu$ or more, more preferably $10\mu$ or more.

An absorbent article comprising the above defined leakproof sheet is unexpectedly improved in flexibility, prevention of stuffiness and rashes and durability for use.

The other members of the absorbent article of this invention will now be described.

A linear kraft pulp wrapped in a tissue is generally used as the absorbent layer. A sheet including a highly water-absorptive polymer incorporated into an absorbent layer as mentioned above, which is devised to enhance the water absorbing effect for holding therein urine or the like absorbed against the weight of a wearer, has recently been employed. In the present invention, an absorbent layer including such a highly water-absorptive polymer incorporated thereinto is preferred.

A nonwoven fabric is mainly employed as the liquid-permeable surface sheet constituting a surface layer to be in contact with the skin. In order to allow the effect of use of a porous film to be more highly exerted in the present invention, a surface sheet devised to prevent a liquid absorbed from returning back from the absorbent layer is preferred. For that purpose, a hydrophobic nonwoven fabric mainly comprising a polyester or polyolefin fiber may be utilized.

Beside the essential members as mentioned above, known auxiliaries such as a pressure-sensitive tape as the fixing member of the absorbent article and a stretchable member attached for developing a leakproof effect may be utilized in the absorbent article of this invention.

EXAMPLES

The following Examples will illustrate the present invention in more detail, but should not be construed as limiting the scope of the invention.

REFERENTIAL EXAMPLE 1

Preparation of Hydrogenated Liquid Polybutadiene

An autoclave having a capacity of 10 l was charged with 3 kg of commercially available liquid polybutadiene (manufactured by Nippon Soda Co., Ltd.; type B 2000, average molecular weight: 2,000), 3 kg of cyclohexane, and 300 g of a catalyst composed of ruthenium (5%) supported on carbon (manufactured by Nippon Engelhard, Ltd.). The system was purged with a purified argon gas. Thereafter, a high-purity hydrogen gas was supplied to the autoclave and at the same time, heating was initiated. Stationary conditions (internal temperature: about 100° C., internal pressure: about 50 kg/cm$^2$) were attained after about 30 minutes.

These conditions were maintained for about 15 hours. The hydrogenation reaction was then stopped. The polymer obtained was a hydrogenated polybutadiene having an iodine value of 4.2 g/100 g, which was liquid at normal temperatures.

REFERENTIAL EXAMPLE 2

Preparation of Polyhydroxy Saturated Hydrocarbon

Substantially the same procedures as in Referential Example 1 except that G-2000 (average molecular weight: 2,000, manufactured by Nippon Soda Co., Ltd.) was used as the liquid polybutadiene. The obtained polymer was a liquid polyhydroxy saturated hydrocarbon having an iodine value of 4.4 g/100 g and a hydroxyl value of 52 mg KOH/g.

EXAMPLE 1

3.4 kg of a high-density polyethylene resin having a melt index of 0.20 g/10 min and a density of 0.949 g/cm$^3$, and 5.8 kg of calcium carbonate (average particle size: 1.2μ, treated with an aliphatic acid in an amount of 2.5 weight parts per 100 weight parts of calcium carbonate) were stirred and mixed in a Henshel mixer. To the resulting mixture was added 0.8 kg of the polyhydroxy saturated hydrocarbon obtained in Referential Example 2, followed by further stirring and mixing. Thus 10 kg of a mixture was obtained. The blending procedure as described above was repeated 5 times to finally obtain 50 kg of a mixture.

The melt index represents an amount of a resin extruded at 190° C. under a load of 2.16 kg in accordance with ASTM D 1238-70, and the density was determined at 20° C. by a density gradient tube method in accordance with ASTM D1505. The mixture thus obtained was kneaded and granulated in a biaxial kneader DSM-65 (manufactured by The Japan Steel Works, Ltd.) The grains thus prepared were subjected to inflation molding with an inflation molding machine equipped with a 50 mmφ extruder to form a film having a thickness of 100μ. The extrusion conditions were as follows:

cylinder temperature: 170°-170°-190° C.
head dice temperature: 190°-190° C.
blow ratio: 3.1

The film thus obtained was longitudinally stretched with a roll stretching, machine and then transversally stretched with a tenter stretching machine. The stretching conditions were as follows:

longitudinal stretching temperature: 75° C.
longitudinal stretching ratio: 2.0
transversal stretching temperature: 105° C.
transversal stretching ratio: 3.0.

The heat treatment was effected at a temperature of 110° C. and at a rate of relaxation in the transversal direction of 10% after the transversal stretching.

The obtained film was a uniformly whitened porous film having a thickness of 43μ, a pore volume of 0.44 cm$^3$ per unit volume of a film of 1 cm$^3$, an average pore size of micropores of 0.38μ, a water vapor permeability of 5,800 g/m$^2$·24 hr, an Elemendorf tear strength in the longitudinal direction of the film of 20 kg cm/cm$^2$, and bending resistances in the longitudinal and transversal directions of the film of as low as 25 mm and 22 mm, respectively, which suggests a very excellent flexibility.

A disposable diaper was prepared by using the porous film thus obtained as the leakproof sheet, stacking fluff pulp in the form of fabric as the absorbent layer at 300 g/m$^2$, superimposing thereon a highly absorbent polymer "Aquakeep" (manufactured by Seitetsu Kagaku Co., Ltd.) which was uniformly sprayed at 70 g/m$^2$ in the middle and wrapped in a moisture-resistant water-absorbent paper, further superimposing a non-woven fabric mainly comprising a hydrophobic fiber, such as a polyethylene-polypropyrene conjugated fiber, ES Fiber, tradename of Chisso Corporation having a basis weight of 20 g/m$^2$, as the surface sheet, molding them into one piece, and attaching a fixing tape thereto.

The diaper thus obtained was soft, and had a good touch and an excellent comfortability.

The measurement methods for evaluation items of the above-mentioned film were as follows.
(a) Pore volume (cm$^3$/cm$^3$) and average pore diameter (μ):

They were measured by using a mercury porosimeter (60,000 psi porosimeter manufactured by Aminco). The pore volume was expressed in terms of accumulative pore volume, per unit volume of a film of 1 cm$^3$, of pores ranging from those of a minute pore size to those of 10$\mu$ in radius in a diagram of accumulative pore volume distribution. The average pore size was expressed in terms of pore radius corresponding to the position of an accumulative pore volume where it assumed a value of half the abovementioned pore volume.

(b) Water vapor permeability (g/m$^2$·24 hr):

It was measured at a temperature of 30° C. at a relative humidity of 90% in accordance with JIS Z 0208-1978.

(c) Elmendorf tear strength (kg·cm/cm$^2$):

It was measured by using an Elmendorf paper tester (manufactured by Toyo Seiki Seisaku-Sho, Ltd.) at a temperature of 20° C. at a relative humidity of 65% in accordance with JIS P 8116.

(d) Bending resistance (mm):

It was measured according to a 45° cantilever method as stipulated in JIS L 1018-1977. The measurement was conducted at a temperature of 20° C. at a relative humidity of 65%.

COMPARATIVE EXAMPLE 1

5.0 kg of the same high-density polyethylene as in Example 1 was blended and kneaded with 5.0 kg of calcium carbonate in the same manner as in Example 1. The composition thus obtained was subjected to inflation molding under the same extrusion conditions as in Example 1 by using an inflation molding machine equipped with a 50 mm$\phi$ extruder to form a film having a thickness of 95$\mu$. The film was longitudinally stretched with a roll and then transversally stretched with a tenter under the same stretching conditions as in Example 1, followed by a heat treatment.

The film thus obtained was a porous film having a thickness of 29$\mu$, a pore volume of 0.20 cm$^3$/cm$^3$, an average pore size of 0.25$\mu$, and a water vapor permeability of 3,400 g/m$^2$·24 hr. The Elmendorf tear strength in the longitudinal direction of the film was 8 kg·cm/cm$^2$. The bending resistances were very high as 61 mm in the longitudinal direction of the film and 52 mm in the transversal direction of the film. Thus the film had problems of tear strength and flexibility.

A disposable diaper was formed by using this porous film as the leakproof film in the same manner as in Example 1.

The diaper thus obtained was inferior in flexibility to that obtained in Example 1. The diaper was apt to tear in the portion just beside the tape.

COMPARATIVE EXAMPLE 2

4.8 kg of the same high-density polyethylene as in Example 1 was stirred and mixed with 4.9 kg of calcium carbonate in the same manner as in Example 1. To the resulting mixture was added 0.3 kg of an epoxidized soybean oil (Adeka Argus Chemical Co., Ltd.; ADK Cizer 0-130L), followed by further stirring and mixing. The resulting mixture was kneaded, granulated, and inflation-molded to form a film having a thickness of 110$\mu$ in the same manner as in Example 1. The film formation conditions were the same as in Example 1. The film was then biaxially stretched under the same stretching conditions as in Example 1, followed by a heat treatment. The porous film thus obtained had a thickness of 35$\mu$, a pore volume of 0.24 cm$^3$/cm$^3$, an average pore size of 0.26$\mu$, and a water vapor permeability of 3,600 g/m$^2$·24 hr. The Elmendorf tear strength in the longitudinal direction of the film was 9 kg cm/cm$^2$. The bending resistances were 59 mm in the longitudinal direction of the film and 54 mm in the transversal direction of the film.

A disposable diaper was formed by using this porous film as the leakproof sheet in the same manner as in Example 1.

The diaper thus obtained was inferior in flexibility to that obtained in Example 1. The diaper was apt to tear just beside the tape.

EXAMPLE 2

3.5 kg of the same high-density polyethylene as in Example 1 was stirred and mixed with 6.0 kg of the same calcium carbonate as in Example 1 in a Henshel mixer. To the resulting mixture were added 0.5 kg of the same polyhydroxy saturated hydrocarbon and 0.3 kg of the same epoxidized soybean oil as in Comparative Example 2, followed by further stirring and mixing. Thus 10.3 kg of a mixture was obtained. Thereafter, the mixture was kneaded, granulated, and inflation-molded to form a film having a thickness of 65$\mu$. The film formation conditions were the same as in Example 1. Subsequently, the film was biaxially stretched in the same manner as in Example 1, followed by a heat treatment. The porous film thus obtained had a thickness of 29$\mu$, a pore volume of 0.49 cm$^3$/cm$^3$, an average pore size of 0.41$\mu$, and a water vapor permeability of 6,500 g/m$^2$·24 hr. The Elmendorf tear strength in the longitudinal direction was 18 kg·cm/cm$^2$. The bending resistances were 19 mm in the longitudinal direction of the film and 18 mm in the transversal direction of the film.

A disposable diaper was formed by using this porous film as the leakproof sheet in the same manner as in Example 1.

The diaper thus obtained was excellent in flexibility and tear strength.

EXAMPLE 3

3.06 kg of linear, low-density polyethylene having a melt index of 1.2 g/10 min and a density of 0.924 g/cm$^3$, and 0.34 kg of high-pressure, low-density polyethylene having a melt index of 2.0 g/10 min and a density of 0.918 g/cm$^3$ were stirred and mixed with 5.8 kg of the same calcium carbonate as in Example 1 in a Henshel mixer. To the resulting mixture was added 0.8 kg of the same polyhydroxy saturated hydrocarbon as in Example 1, followed by further stirring and mixing, to obtain a mixture. Thereafter, the mixture was kneaded and granulated in the same manner as in Example 1, and then inflation-molded to obtain a film having a thickness of 60$\mu$. The film was longitudinally stretched with a roll and then transversally stretched with a tenter, followed by a heat treatment. The stretching conditions were as follows:

longitudinal stretching temperature: 60° C.
longitudinal stretching ratio: 2.0
transversal stretching temperature: 100° C.
transversal stretching ratio: 2.5

The conditions of the heat treatment after the transversal stretching were a temperature of 105° C. and a rate of relaxation in the transversal direction of 8%.

The film thus obtained was a uniformly whitened porous film having a thickness of 34$\mu$, a pore volume of 0.55 cm$^3$/cm$^3$, an average pore size of 0.51$\mu$, and a water vapor permeability of 7,700 g/m$^2$·24 hr. The Elmendorf tear strength in the longitudinal direction of the film was 25 kg·cm/cm$^2$. The bending resistances were 23 mm in the longitudinal direction of the film and 21 mm in the transversal direction of the film.

A disposable diaper was formed by using this porous film as the leakproof sheet in the same manner as in Example 1.

The diaper thus obtained was excellent in tear strength and flexibility.

EXAMPLE 4

3.69 kg of the same linear, low-density polyethylene as in Example 3, and 0.41 kg of high-pressure, low-density polyethylene were stirred and mixed with 5.1 kg of calcium carbonate in a Henshel mixer. To the resulting mixture were added 0.5 kg of the same polyhydroxy saturated hydrocarbon as in Example 1 and 0.3 kg of the same epoxidized soybean oil as in Comparative Example 2, followed by further stirring and mixing. The resulting mixture was kneaded and granulated in the same manner as in Example 1, and inflation-molded in the same manner as in Exmaple 1 to form a film having a thickness of 60μ. The film was biaxially stretched and heat-treated in substantially the same manner as in Example 3 except that the longitudinal stretching ratio was 2.5 and the transversal stretching ratio was 3.

The obtained film was a porous film having a thickness of 26μ, a pore volume of 0.53 cm$^3$/cm$^3$, an average pore size of 0.47μ, and a water vapor permeability of 7,000 g/m$^2$·24 hr. The Elmendorf tear strength in the longitudinal direction of the film was 17 kg·cm/cm$^2$. The bending resistances were 18 mm in the longitudinal direction of the film and 18 mm in the transversal direction of the film.

A disposable diaper was formed by using this porous film as the leakproof sheet in the same manner as in Example 1.

The diaper thus obtained was excellent in flexibility.

EXAMPLE 5

A film having a thickness of 55μ was formed from the composition used in Example 4 according to inflation molding conducted in substantially the same manner as in Example 1 except that the blow ratio in extrusion was 1.2. The film was longitudinally stretched with a roll at a stretching temperature of 80° C. with a stretching ratio of 2.4, and then transversely stretched by using a tubular extruder, followed by a heat treatment with a roll. The transversal stretching conditions were a stretching temperature of 90° C. and a stretching ratio of 2.5. The heat treatment conditions were a temperature of 95° C. and a rate of relaxation in the longitudinal direction of the film of 10%.

The obtained film was a uniformly whitened beautiful porous film having a thickness of 34μ. a pore volume of 0.33 cm$^3$/cm$^3$, an average pore size of 0.31μ, and a water vapor permeability of 4,700 g/m$^2$·24 hr. The Elmendorf tear strength in the longitudinal direction of the film was 56 kg·cm/cm$^2$. The bending resistances were 16 mm in the longitudinal direction of the film and 15 mm in the transversal direction of the film.

A disposable diaper was formed by using this porous film as the leakproof sheet in the same manner as in Example 1.

The diaper thus obtained was excellent in tear strength and flexibility.

EXAMPLE 6

3.87 kg of the same linear, low-density polyethylene as in Example 3, and 0.43 kg of high-pressure, low-density polyethylene were stirred and mixed with 4.9 kg of calcium carbonate as in Example 1 in a Henshel mixer. Subsequently, 0.8 kg of the hydrogenated liquid polybutadiene obtained in Referential Example 1 was added to the mixture, followed by further stirring and mixing, to obtain a mixture. The mixture was kneaded and granulated in the same manner as in Example 1, and then subjected to T-die extrusion molding with a 65 mmφ extruder to form a film having a thickness of 60μ. The T-die extrusion conditions were as follows:

cylinder temperature: 170°-190°-210° C.
adapter, dice temperature: 210°-210° C.
cooling roll surface temperature: 60° C.

T-die used had a lip width of 1,000 mm and lip clearence of 1.2 mm. The film was longitudinally stretched with a roll at a stretching temperature of 80° C. with a stretching ratio of 1.5, and then transversally stretched with a tenter at a stretching temperature of 113° C. with a stretching ratio of 2.3, followed by a heat treatment conducted at a temperature of 115° C. and at a rate of relaxation in the transversal direction of the film of 13%.

The obtained porous film had a thickness of 33μ, a pore volume of 0.23 cm$^3$/cm$^3$, an average pore size of 0.22μ, and a water vapor permeability of 2,900 g/m$^2$·24 hr. The Elmendorf tear strength in the longitudinal direction was 35 kg cm/cm$^2$. The bending resistances were 22 mm in the longitudinal direction of the film and 20 mm in the transversal direction of the film.

A disposable diaper was formed by using this porous film as the leakproof sheet in the same manner as in Example 1.

The diaper thus obtained was excellent in longitudinal tear strength and flexibility.

COMPARATIVE EXAMPLE 3

A film having a thickness of 65μ was obtained by inflation molding in substantially the same manner as in Example 3 except that the same hydrogenated liquid polybutadiene as in Example 6 was used instead of the polyhydroxy saturated hydrocarbon used in Example 3. The film was monoaxially stretched with a roll at a stretching temperature of 60° C. with a stretching ratio of 3.5, followed by a heat treatment conducted at a temperature of 100° C. and a rate of relaxation in the longitudinal direction of the film of 10%.

The obtained porous film had a thickness of 37μ, a pore volume of 0.35 cm$^3$/cm$^3$, an average pore size of 0.27μ, and a water vapor permeability of 4,900 g/m$^2$·24 hr. The Elmendorf tear strength in the longitudinal direction of the film was 2 kg·cm/cm$^2$. The bending resistances were 18 mm in the longitudinal direction of the film and 19 mm in the transversal direction of the film.

A disposable diaper was formed by using this porous film as the leakproof sheet in the same manner as in Example 1.

The diaper thus obtained was flexible but so low in longitudinal tear strength as to be very liable to tear.

The test results of Examples 1 to 6 and Comparative Examples 1 to 3 described above are summarized in Table 1.

In Table 1, the flexibility of a diaper was evaluated in accordance with the following standards:

⊚ : the leakproof sheet is very soft, and the feeling of the diaper is very good;
◯: the leakproof sheet is soft, and the feeling of the diaper is good; and
X: the leakproof sheet is starchy and stiff, and the diaper gives a stiff feeling.

TABLE 1

| | Thickness μ | Average pore diameter, μ | Pore volume cm³/cm³ | Water vapor permeability g/m²·24 hr | Tear strength kg·cm/cm² | Bending resistance MD mm | Bending resistance CD mm | Flexibility of diaper | Rate of tear in a region in contact with tape* % |
|---|---|---|---|---|---|---|---|---|---|
| Example 1 | 43 | 0.38 | 0.44 | 5800 | 20 | 25 | 22 | ◯ | 0.5 |
| Example 2 | 29 | 0.41 | 0.49 | 6500 | 18 | 19 | 18 | ⊚ | 1.0 |
| Example 3 | 34 | 0.51 | 0.55 | 7700 | 25 | 23 | 21 | ◯ | 0.5 |
| Example 4 | 26 | 0.47 | 0.53 | 7000 | 17 | 18 | 18 | ⊚ | 1.0 |
| Example 5 | 34 | 0.31 | 0.33 | 4700 | 56 | 16 | 15 | ⊚ | 0 |
| Example 6 | 33 | 0.22 | 0.23 | 2900 | 35 | 22 | 20 | ◯ | 0 |
| Comp. Ex. 1 | 29 | 0.25 | 0.20 | 3400 | 8 | 61 | 52 | X | 12.0 |
| Comp. Ex. 2 | 35 | 0.26 | 0.24 | 3600 | 9 | 59 | 54 | X | 10.5 |
| Comp. Ex. 3 | 37 | 0.27 | 0.35 | 4900 | 2 | 18 | 19 | ⊚ | 35.5 |

(Note)
*Wearing test: 20 disposable diapers formed are worn by each of 10 infant monitors to observe occurrence or non-occurrence of tear in a region in contact with the tape. The rate of torn diapers relative to the total diapers is shown.

EXAMPLE 7

3.4 kg of a high-density polyethylene resin having a melt index of 0.20 g/10 min and a density of 0.949 g/cm³, and 6.1 kg of calcium carbonate (average particle size: 1.0μ, treated with an aliphatic acid) were stirred and mixed in a Henshel mixer. To the resulting mixture was added 0.6 kg of the polyhydroxy saturated hydrocarbon obtained in Referential Example 2, followed by further stirring and mixing. Thus 10 kg of a mixture was obtained. The blending procedure as described above was repeated 5 times to finally obtain 50 kg of a mixture.

The melt index represents an amount of a resin extruded at 190° C. under a load of 2.16 kg in accordance with ASTM D 1238-70, and the density was determined at 20° C. by a density gradient tube method in accordance with ASTM D1505. The mixture thus obtained was kneaded and granulated in a biaxial kneader DSM-65 (manufactured by The Japan Steel Works, Ltd.). The grains thus prepared were subjected to inflation molding with an inflation molding machine equipped with a 50 mmφ extruder to form a film having a thickness of 70μ. The extrusion conditions were as follows:
cylinder temperature: 170°-170°-190° C.
head dice temperature: 190°-190° C.
blow ratio: 3.1

The film thus obtained was longitudinally stretched with a roll stretching machine. The stretching conditions were as follows:
longitudinal stretching temperature: 75° C.
stretching ratio: 3.0.

The heat treatment was effected at a temperature of 100° C. and at a rate of relaxation in the transversal direction of 10% after the transversal stretching.

The obtained film was a uniformly whitened porous film having a thickness of 46μ, a pore volume of 0.30 cm³ per unit volume of a film of 1 cm³, an average pore size of micropores of 0.33μ, a water vapor permeability of 4,100 g/m²·24 hr., and bending resistances in the longitudinal and transversal directions of the film of as low as 22 mm and 21 mm, respectively, which suggests excellent flexibility.

A disposable diaper was prepared by using the porous film thus obtained as the leakproof sheet, stacking fluff pulp in the form of fabric as the absorbent layer at 300 g/m², superimposing thereon a highly absorbent polymer "Aquakeep" (manufactured by Seitetsu Kagaku Co., Ltd.) which was uniformly sprayed at 70 g/m² in the middle and wrapped in a moisture-resistant water-absorbent paper, further superimposing a non-woven fabric mainly comprising a hydrophobic fiber, especially ES Fiber, tradename of Chisso Corporation as shown before, as the surface sheet, molding them into one piece, and attaching a fixing tape thereto.

The diaper thus obtained was soft, and had a good touch and an excellent comfortability.

COMPARATIVE EXAMPLE 4

5.0 kg of the same high-density polyethylene as in Example 7 was blended and kneaded with 5.0 kg of calcium carbonate in the same way as in Example 7. The composition thus obtained was subjected to inflation molding under the same extrusion conditions as in Example 7 by using an inflation medium machine equipped with a 50 mmφ extruder to form a film having a thickness of 95μ. The film was longitudinally stretched with a roll.

The stretching conditions are as follows.
stretching temperature: 100° C.
stretching ratio: 5.5

The heat treatment was conducted at 110° C. and at a rate of relaxation, in the longitudinal direction, of 10%.

The film thus obtained was a porous film having a thickness of 35μ, a pore volume of 0.22 cm³/cm³, an average pore size of 0.28μ, and a water vapor permeability of 3,300 g/m²·24 hr. The bending resistances were as very high as 63 mm in the longitudinal direction of the film and 80 mm in the transversal direction of the film. Thus the film involved a problem of flexibility.

A disposable diaper was formed by using this porous film as the leakproof film in the same manner as in Example 7.

The diaper thus obtained was inferior in flexibility to that obtained in Example 7.

EXAMPLE 8

3.5 kg of the same high-density polyethylene as in Example 7 was stirred and mixed with 6.0 kg of the same calcium carbonate as in Example 7 in a Henshel mixer. To the resulting mixture were added 0.5 kg of the same polyhydroxy saturated hydrocarbon as in Example 7 and 0.3 kg of an epoxidized soybean oil (Adeka Argus Chemical Co., Ltd.; ADK Cizer 0-130L), followed by further stirring and mixing. Thus 10.3 kg of a mixture was obtained. Therefore, the mixture was kneaded, granulated, and inflation-molded to form a film having a thickness of 70μ. The film formation conditions were the same as in Example 7. Then, the film was monoaxially stretched under the following conditions.

Stretching Conditions
stretching temperature: 75° C.
stretching ratio: 2.0

The porous film thus obtained had a thickness of 51μ, a pore volume of 0.18cm$^3$/cm$^3$, an average pore size of 0.14μ, and water vapor permeability of 2,000g/m$^2$·24 hr. The bending resistances were 28 mm in the longitudinal direction of the film and 29 mm in the transversal direction of the film.

A disposable diaper was formed by using this porous film as the leakproof sheet in the same manner as in Example 7.

The diaper thus obtained was excellent in flexibility.

EXAMPLE 9

3.15 kg of linear, low-density polyethylene having a melt index of 1.2 g/10 min and a density of 0.924 g/cm$^3$, and 0.35 kg of high-pressure, low-density polyethylene having a melt index of 2.0 g/10 min and a density of 0.918 g/cm$^3$ were stirred and mixed with 6.0 kg of the same calcium carbonate as in Example 7 in a Henshel mixer. To the resulting mixture was added 0.8 kg of the same polyhydroxy saturated hydrocarbon as in Example 7 and 0.2 kg of the same epoxidized soybean oil as in Example 8, followed by further stirring and mixing, to obtain a mixture. Thereafter, the mixture was kneaded and granulated in the same manner as in Example 7, and then inflation-molded to obtain a film having a thickness of 45μ. The film was longitudinally stretched with a roll, followed by a heat treatment. The stretching conditions were as follows:

stretching temperature: 60° C.
stretching ratio: 4.0

The conditions of the heat treatment are the same as in Example 7.

The film thus obtained was a uniformly whitened porous film having a thickness of 24μ, a pore volume of 0.49 cm$^3$/cm$^3$, an average pore size of 0.31μ, and a water vapor permeability 400g/m$^2$·24 hr. The bending resistances were 17 mm in the longitudinal direction of the film and 15 mm in the transversal direction of the film. Thus it was a flexible porous film.

A disposable diaper was formed by using this porous film as the leakproof sheet in the same manner as in Example 7.

The diaper thus obtained was excellent in flexibility.

EXAMPLE 10

3.4 kg of the same linear, low-density polyethylene as in Example 9 was stirred and mixed with 5.9 kg of calcium carbonate and 0.7 kg of a polyhydroxy saturated hydrocarbon in a Henshel mixer. The resulting mixture was kneaded and granulated in the same manner as in Example 7, and inflation-molded in the same manner as in Example 7 to form a film having a thickness of 38μ.

The film was monoaxially stretched with a roll at a stretching ratio of 2.5. The heat treatment was conducted under the same conditions as in Example 7.

The obtained film was a porous film having a thickness of 27μ, a pore volume of 0.30 cm$^3$/cm$^3$, an average pore size of 0.28μ, and a water vapor permeability of 4,900 g/m$^2$·24 hr. The bending resistances were 16 mm in the longitudinal direction of the film and 13 mm in the transversal direction of the film.

A disposable diaper was formed by using this porous film as the leakproof sheet in the same manner as in Example 7.

The diaper thus obtained was excellent in flexibility.

EXAMPLE 11

3.1 kg of the same linear, low-density polyethylene as in Example 9, and 0.3 kg of high pressure, low-density polyethylene having a melt index of 0.5 g/10 min and a density of 0.922 g/cm$^3$ were stirred and mixed with 5.9 kg of calcium carbonate as in Example 7 in a Henshel mixer. Subsequently, 0.7 kg of the hydrogenated liquid polybutadiene obtained in Referential Example 1 was added to the mixture, followed by further stirring and mixing, to obtain a mixture. The mixture was kneaded, granulated, and inflation-molded to form a film having a thickness of 40μ. Subsequently, monoaxial stretching was conducted with a roll at a stretching temperature of 60° C. and at a stretching ratio of 3.5, followed by a heat treatment. The heat treatment conditions were the same as in Example 7.

Stretched with a tenter at a stretching temperature of 113° C. with a stretching ratio of 2.3, followed by a heat treatment conducted at a temperature of 115° C. and at a rate of relaxation in the transversal direction of the film of 13%.

The obtained porous film had a thickness of 25μ, a pore volume of 0.40 cm$^3$/cm$^3$, an average pore size of 0.23μ, and a water vapor permeability of 5,200 g/m$^2$·24 hr. The bending resistances of the film were 15 mm in the longitudinal direction of the film and 14 mm in the transversal direction of the film.

A disposable diaper was formed by using this porous film as the leakproof sheet in the same manner as in Example 7.

The diaper thus obtained was excellent in flexibility.

Test results of Examples 7 to 11 and Comparative Example 4 are shown in Table 2.

In order to evaluate the resistance to weather involving NOx, the test of yellowing with NOx was conducted.

Whiteness (W term) and yellowness (Δb term) in an NOx unit number of 3 were measured (JIS Z8722).

TABLE 2

| | Thickness μ | Average pour diameter μ | Pour volume cm$^3$/cm$^3$ | Water vapor permeability g/m$^2$ · 24 hr | Bending resistance | | Flexibility of diaper | Whiteness (W term) | Yellowness (Δb term) |
|---|---|---|---|---|---|---|---|---|---|
| | | | | | MD mm | CD mm | | | |
| Example 7 | 46 | 0.33 | 0.30 | 4100 | 22 | 21 | ○ | 90.3 | 4.1 |
| Example 8 | 51 | 0.14 | 0.18 | 2000 | 28 | 29 | ○ | 92.1 | 2.9 |
| Example 9 | 24 | 0.31 | 0.49 | 5400 | 17 | 15 | ⊚ | 92.3 | 3.0 |
| Example 10 | 27 | 0.28 | 0.30 | 4900 | 16 | 13 | ⊚ | 90.2 | 4.2 |
| Example 11 | 25 | 0.23 | 0.40 | 5200 | 15 | 14 | ⊚ | 90.3 | 4.1 |
| Comp. Example 4 | 35 | 0.28 | 0.22 | 3300 | 60 | 80 | X | 90.5 | 4.2 |

The embodiments of the invention in which an exclusive property or privilege is claimed are defined as follows:

1. An absorbent article comprising a liquid-impermeable, leakproof sheet; a liquid-permeable sheet; and an absorbent layer provided between said leakproof sheet and said surface sheet, wherein said leakproof sheet is a monoaxially or biaxially stretched porous film of a polyolefin resin composition comprising 100 parts by weight of a polyolefin, 25 to 400 parts by wight of a filler, 1 to 100 parts by weight of a liquid or wax hydrocarbon polymer and 3 to 70 parts by weight of an epoxy group containing organic compound said film having a pore size of 0.05 to 5 microns, a pore volume of not smaller than 0.1 cm$^3$/cm$^3$, a water vapor permeability of not smaller than 500 g/m$^2$ for 24 hours and a bending resistance in the longitudinal and transversal direction which satisfies the following formula:

$$\text{bending resistance} \leq 0.193 \times \text{film thickness} + 35$$

wherein bending resistance is in mm, and film thickness is in $\mu$.

2. An absorbent article as claimed in claim 1, in which said leakproof sheet has an Elmendorf tear strength in the longitudinal direction of not smaller than 15 kg·cm/cm$^2$.

3. An absorbent article as claimed in claim 1, in which said leakproof sheet has been biaxially stretched and has a thickness of not larger than 45 microns and an Elmendorf tear strength in the longitudinal direction of not smaller than 15 kg·cm/cm$^2$.

4. An absorbent article as claimed in claim 1, in which said leakproof sheet has been monoaxially stretched.

5. An absorbent article as claimed in claim 1 wherein said hydrocarbon is selected from the group consisting of polybutadiene, polybutene, polyisoprene and derivatives thereof.

6. An absorbent article as claimed in claim 5 wherein said polybutadiene is a liquid hydrogenated polybutadiene.

7. An absorbent article as claimed in claim 5 wherein said polybutadiene has terminal carboxyl or hydroxyl groups.

8. An absorbent article as claimed in claim 7 wherein said hydroxy groups are modified with radicals selected from the group consisting of an epoxy group, an isocyanate group and maleic anhydride.

9. An absorbent article as claimed in claim 1 wherein said epoxy group-containing organic compound is selected from the group consisting of epoxidized linseed oil, epoxidized soybean oil and epoxy resins.

* * * * *